US007340384B2

(12) United States Patent
Delhomme et al.

(10) Patent No.: US 7,340,384 B2
(45) Date of Patent: Mar. 4, 2008

(54) PROCESS FOR DETERMINING THE VARIATION IN THE RELATIVE PERMEABILITY OF AT LEAST ONE FLUID IN A RESERVOIR

(75) Inventors: Jean-Pierre Delhomme, Boulogne Billancourt (FR); Yves Manin, Le Plessis Robinson (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 761 days.

(21) Appl. No.: 10/065,684

(22) Filed: Nov. 8, 2002

(65) Prior Publication Data
US 2003/0088391 A1 May 8, 2003

(30) Foreign Application Priority Data
Nov. 8, 2001 (FR) .................................. 01 14447

(51) Int. Cl.
G06G 7/48 (2006.01)
G06G 7/50 (2006.01)
E21B 49/00 (2006.01)
E21B 47/00 (2006.01)

(52) U.S. Cl. .................. 703/10; 73/152.06; 73/152.08; 166/250.1

(58) Field of Classification Search .................... 703/2, 703/10, 9; 166/250.01, 250.1; 73/152.06, 73/152.08
See application file for complete search history.

(56) References Cited

U.S. PATENT DOCUMENTS
4,672,588 A * 6/1987 Willen .......................... 367/28
(Continued)

FOREIGN PATENT DOCUMENTS
EP 0 656 547 A1 6/1995
WO WO 01/11391 A1 2/2001

OTHER PUBLICATIONS
Akbar, M. et al. "Classic Interpretation Problems: Evaluating Carbonates". Oilfield Review. Jan. 1995. pp. 38-57.*
(Continued)

Primary Examiner—Paul Rodriguez
Assistant Examiner—Ayal Sharon
(74) Attorney, Agent, or Firm—Matthias Abiel; James Kurka; Bryan White

(57) ABSTRACT

A method for determining for a reservoir (1) containing fluids (W, O), the variation in the relative permeability (krO, krW) of at least one of the fluids, as a function of the saturation of at least one of the fluids (W, O),) is provided. According to this method a saturation distribution of one of the fluids of the reservoir is determined on the basis of a measurement of a physical property in the reservoir. A dynamic model (20) for the flow of fluids in the reservoir (1) is created. The dynamic model generates a saturation distribution. The saturation distribution (40) generated by the dynamic model is compared with saturation distribution obtained from measurement. The dynamic model (20) is updated with intermediate relative permeability values $(krO)_i$ and $(krW)_i$ and steps b and c are repeated if the saturation distribution generated by the dynamic model and that determined on the basis of measurement do not coincide.

14 Claims, 5 Drawing Sheets

U.S. PATENT DOCUMENTS

| | | | |
|---|---|---|---|
| 5,335,542 A * | 8/1994 | Ramakrishnan et al. | 73/152.08 |
| 5,663,499 A * | 9/1997 | Semmelbeck et al. | 73/152.06 |
| 5,963,037 A | 10/1999 | Brady et al. | |
| 6,061,634 A * | 5/2000 | Belani et al. | 702/12 |
| 6,283,210 B1 * | 9/2001 | Soliman et al. | 166/270 |
| 6,405,796 B1 * | 6/2002 | Meyer et al. | 166/249 |
| 6,493,632 B1 * | 12/2002 | Mollison et al. | 702/2 |
| 6,549,879 B1 * | 4/2003 | Cullick et al. | 703/10 |
| 6,711,502 B2 * | 3/2004 | Mollison et al. | 702/6 |
| 6,980,940 B1 * | 12/2005 | Gurpinar et al. | 703/10 |
| 2002/0013687 A1 * | 1/2002 | Ortoleva | 703/10 |

OTHER PUBLICATIONS

Cope. G. "Improving Efficiency Through Reservoir Modelling and Production Simulation." Journal of Canadian Petroleum Technology. Apr. 2001. vol. 40, No. 4. pp. 7-11.*

HN Man and XD Jing, "Pore Network Modeling of Electrical Resistivity and Capillary Pressure Characteristics," *Transport in Porous Media*, Ch. 41, pp. 263-286, Kluwer Academic Publishers, the Netherlands (2000).

* cited by examiner

PROCESS FOR DETERMINING THE VARIATION IN THE RELATIVE PERMEABILITY OF AT LEAST ONE FLUID IN A RESERVOIR

CROSS REFERENCE TO RELATED APPLICATIONS

This application claims the benefit under 35 U.S.C. 119 of French Patent Application No. 01 14447, filed Nov. 8, 2001.

BACKGROUND OF INVENTION

1. Field of the Invention

The present invention is generally related to the hydrodynamic study of subsoil. In particular, the present invention is related to extraction of hydrocarbons.

2. Description of Related Art

Hydrocarbons are present and move about in porous rock formations called reservoirs. In addition to the fluid that one wants to extract, at least one auxiliary fluid is present in a reservoir of hydrocarbons. The fluid that one wants to extract may be oil or gas, while the auxiliary fluid is generally water. The auxiliary fluid may be naturally found in very small quantities in the rock formations of the reservoir. The term given to this residual water is connate water, but in this case it is immobile. It can also be present in larger quantities in the form of an underground water table, which moves during extraction.

Water may also come from a water injection well and may be used in the oil deposit to drive the hydrocarbons towards a production well. This injected auxiliary fluid maintains or restores the pressure in the deposit. This technique of injecting an auxiliary fluid is often used in the initial stages of oil extraction.

The production of a reservoir depends not only on the static characteristics of the reservoir, such as its dimensions and the type of porous rocks in which the hydrocarbons are found, but also on the dynamic characteristics, as the fluids present move within the reservoir towards the well during extraction. The flow of a first fluid O, in a reservoir containing a second fluid W, is governed, amongst other things, by the effective permeability kefO to the first fluid O. This is obtained from the absolute permeability k of the reservoir saturated in the first fluid O multiplied by a correction factor, which is called the relative permeability krO to the first fluid O in the presence of the second fluid W. This order of magnitude characterises the ease with which the first fluid O, in the presence of the second fluid W, passes through the rock formation in the reservoir.

Nowadays, before taking the decision to work on a new hydrocarbon reservoir, its behaviour is simulated by a computer system using a dynamic model for the flow of the fluids in the reservoir. The dynamic model is constructed in three dimensions with a plurality of simulation units, which are cubes whose average edge size is around ten or so metres. It is important to know as accurately as possible, in particular to carry out the simulation, the variation in the relative permeability krO, krW to at least one of the fluids O, W as a function of the saturation S(W) or S(O) in one of the fluids O or W respectively. The saturation of a rock in one fluid is the fraction of the effective volume of the pores of the rock that is taken up by the respective fluid.

In practice, one of the fluids O in the reservoir is an oil or gas hydrocarbon and the other W is water and it is generally the saturation in water S(W) that is used as a parameter. To construct the dynamic flow model, one needs to know the static characteristics of the reservoir. To do this, one begins by constructing a static model of the reservoir that takes into account the geometric measurements of the reservoir and the geological characteristics of the subsoil. These measurements may be carried out by well logging. The dynamic flow model uses the static model of the reservoir, into which one integrates the basic effective permeability kefO to one of the fluids O, the one which one wishes to extract, in the presence of a residual amount of another fluid W.

In practice, one uses the basic effective permeability to the oil or gas in the presence of residual water. This effective permeability kefO is traditionally obtained by way of a pressure build up test. In this type of test, with the reservoir being traversed by at least one well, one begins to extract the fluid O at a certain flow rate, then the production is stopped and the build up in pressure caused by closing the well is measured. The effective permeability kefO is then deduced from this.

In order to make the dynamic model work, it has to be initialised. To do this, one introduces the flow rate and/or pressure figures expected for the reservoir while it is being worked.

The dynamic model is also initialised with the relative permeability values to each of the fluids as a function of the saturation in one of the fluids. In order for the simulation to be reliable, these relative permeability values must be as accurate as possible. The relative permeability values to each of the fluids may be taken from collections of data concerning the reservoir in question, as this data exists for most of the areas involved in oil and gas prospecting. But in this case, it involves average relative permeability values. In terms of accuracy, it is better to carry out permeability analyses in the laboratory, using well cores taken from the reservoir formation. These well cores are solid cylinders, with a diameter of around 10 centimetres, which are extracted from the subsoil. The saturation measurements are not generally carried out on full well cores but on small samples taken from the well cores. While they are being extracted, these well cores can be subjected to irreversible mechanical stresses, caused by the cutting tool, which can modify their relative permeability. Furthermore, while they are being brought up, they can go through, and become impregnated with, mud, which also changes their relative permeability. In general, the relative permeability values obtained in the laboratory are not then the same as the real relative permeability values, which exist in situ in the reservoir formation.

In addition, the relative permeability values obtained from these small samples must be extrapolated so that they fit the scale of the simulation units, which introduces another source of error. With all this imprecision in the relative permeability values, there is a risk that the dynamic model does not provide a correct representation of the flow of fluids contained within the reservoir at the scale of the simulation units.

SUMMARY OF INVENTION

Summary of the Invention

The present invention provides in one embodiment a method of determining for a reservoir (1) containing fluids (W, O), the variation in the relative permeability (krO, krW) of at least one of the fluids, as a function of the saturation of at least one of the fluids (W, O),). According to this method a saturation distribution of one of the fluids of the reservoir is determined on the basis of a measurement of a physical property in the reservoir. A dynamic model (20) for the flow of fluids in the reservoir (1) is created. The dynamic model generates a saturation distribution. The saturation distribution (40) generated by the dynamic model is compared with saturation distribution obtained from measurement. The dynamic model (20) is updated with intermediate relative permeability values $(krO)_i$ and $(krW)_i$ and steps b and c are repeated if the saturation distribution generated by the dynamic model and that determined on the basis of measurement do not coincide.

BRIEF DESCRIPTION OF DRAWINGS

The present invention will be more clearly understood by reading the description of the examples of embodiments, given purely by way of indication and in no way limiting, and by referring to the drawings, in which.

DETAILED DESCRIPTION

Figure 1A:
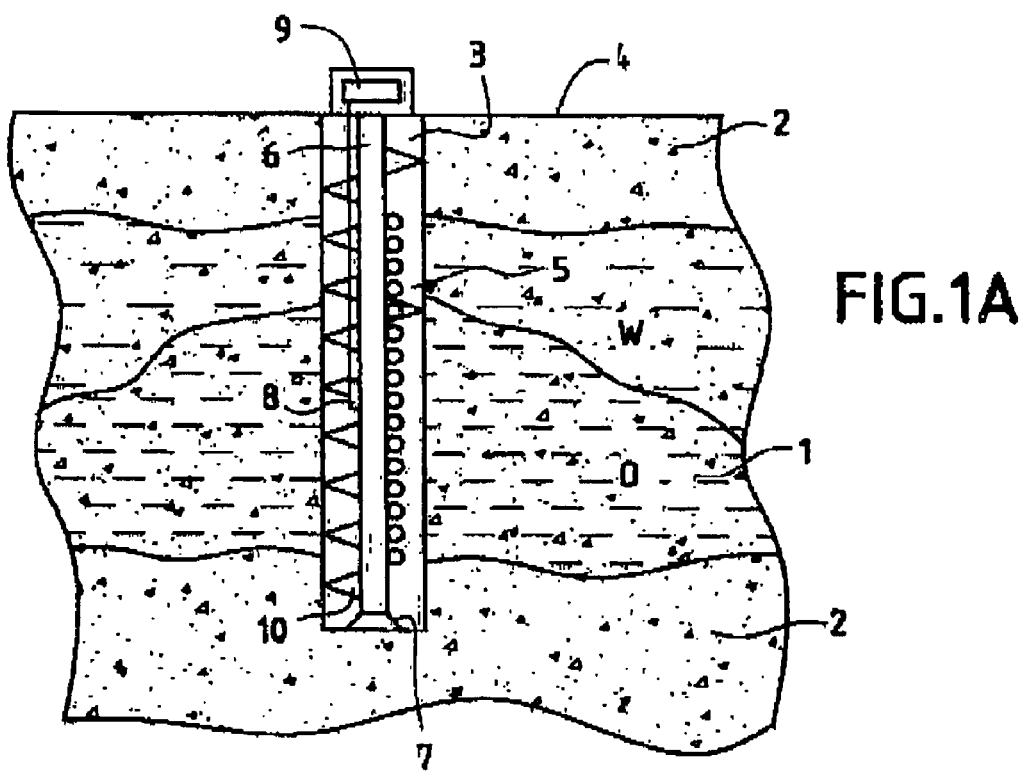
FIG. 1A is a cross section of a reservoir to which the process for determining the variation in the relative permeability and the process for constructing a dynamic flow model, according to the invention, may be applied.

We will now refer to FIG. 1A, which shows a cross-section of a hydrocarbon reservoir 1, to which the process for determining the variation in the relative permeability and the process for constructing a dynamic flow model, according to one embodiment of the present invention, may be applied. Reservoir 1 is located in terrestrial formations 2. A well 3 is bored into the terrestrial formations and passes through the reservoir 1.

Figure 1B:
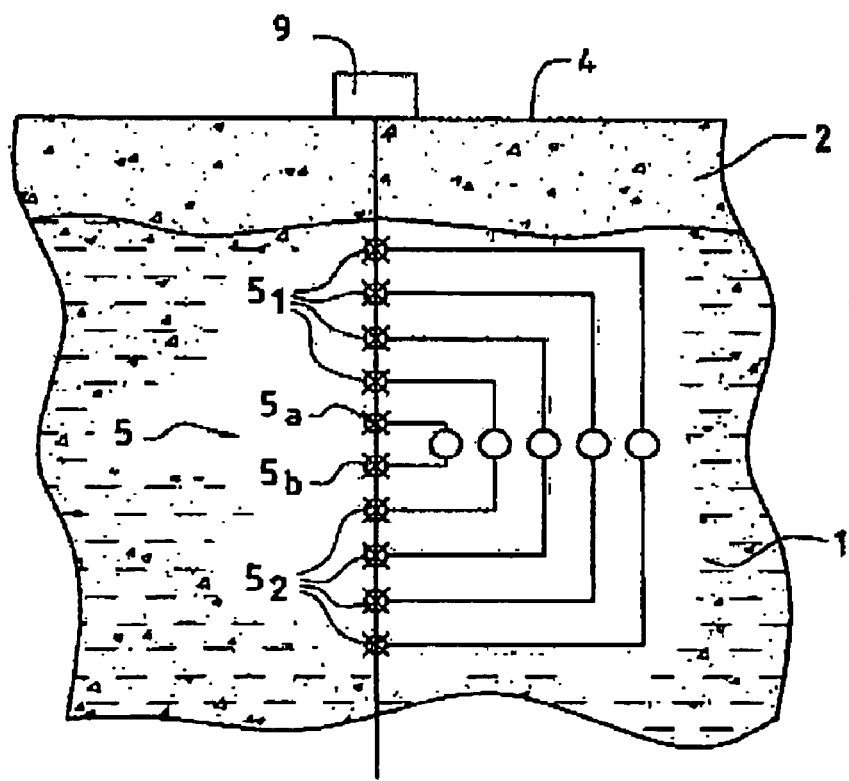
FIG. 1B shows a detail of the instrumentation in a well traversing the reservoir.

FIG. 1B shows a schematic detail of the well 3. This well 3 may be a hydrocarbon extraction well and/or a well for injecting and/or a well of carrying out measurements. It is assumed, in the example described, that it is a water injection well equipped with instrumentation. The well opens out onto the surface of the ground 4. It can have a depth varying from several hundred metres to several kilometres. The reservoir 1 contains a first fluid O that is to be extracted, such as for example oil or gas hydrocarbons, and at least one other fluid W, which is injected into or is naturally found within the reservoir.

The well 3 traditionally contains a well casing 6 and the inside end of the casing is equipped with a casing shoe 7, which protects it and helps it descend. The well 3 has instrumentation comprising at least one network of electrodes, made up, for example, of at least one electrode 5-1 for feeding a current into the reservoir formation, at least one electrode 5-2 for the current return, and several measurement electrodes 5-a and 5-b. The network electrodes 5 are in electrical contact with the interior wall of the well 3, and they are generally fixed to the exterior wall of the casing 6, but are electrically isolated if the casing 6 is an electrical conductor.

One may, for example, measure the potential difference V between two measurement electrodes 5-a and 5-b, while a known current I is fed into the reservoir formation between the feed electrode 5-1 and the return electrode 5-2. FIG. 1B shows a schematic diagram of an example of how the electrodes in the network 5 can be laid out. The two central electrodes act as measurement electrodes and the others, 5-1 and 5-2, paired by a couple, allow one to feed current into the reservoir and the other to return the current, for the different spaces between these electrodes. In fact, the electrodes could alternately play the role of feed electrode and return electrode or measurement electrode.

Instead of carrying out potential measurements, one could carry out current measurements by applying the known potentials of the electrodes. The instrumentation of the wells may also be as described in the French patent application FR A1 2712627 for example. Obviously, other electrode layouts may be used.

In one embodiment of the processes according to the present invention, one of the fluids W (in the example, water) is injected into the reservoir formation 1. The injection is performed into the casing 6 and the fluid W flows up to the interior wall of the well 3 through orifices or perforations in the casing 6.

Figure 2:
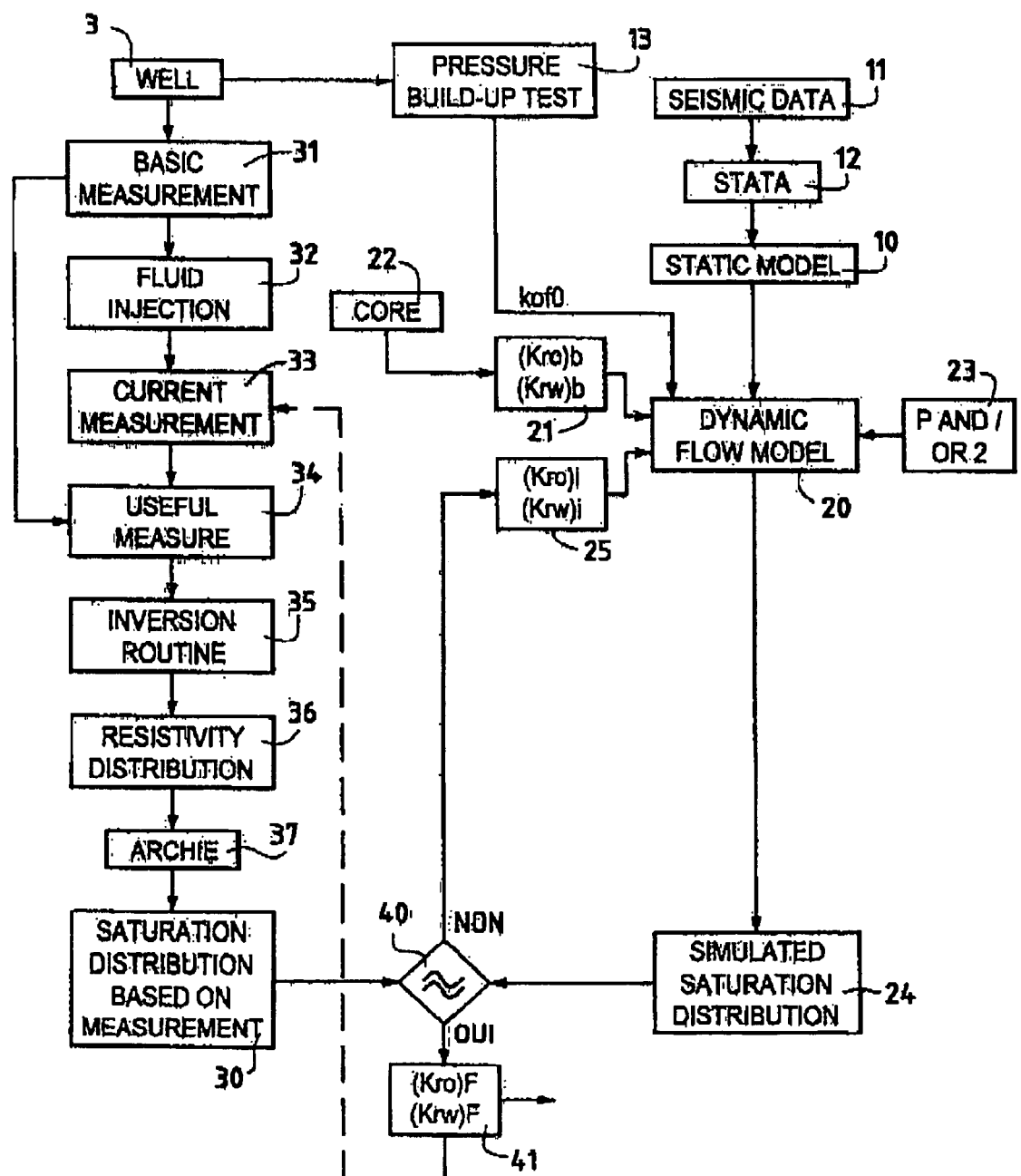
FIG. 2 is a block diagram showing an example of the process for determining the variation in the relative permeability and the process for constructing a dynamic flow model, according to the invention.

FIG. 2 shows a flow chart in connection with one embodiment of the process of determining the variation in the relative permeability of at least one fluid O in the reservoir as a function of the saturation of the reservoir in one of the fluids O or W. This flow chart also applies to the process for constructing a dynamic flow model (dynamic model) for the fluids in the reservoir.

A dynamic model (20) for the flow of fluids in the reservoir (1) is created as follows. One begins by constructing a static model of the reservoir (block 10). This static model (block 10) of the reservoir takes into account the structure of the reservoir with the different strata that make up the reservoir (block 12). The structure of the reservoir is obtained from the geometrical and geological data such as its dimensions, the type of rock strata that make up the reservoir and their porosity. The geometrical and geological data is obtained, for example, by interpreting core logging measurements and/or seismic data (block 11) carried out in the reservoir formations.

The dynamic model (block 20) of the reservoir also integrates the effective permeability kefO to one of the fluids O, the fluid that one wants to extract, at the residual saturation in another fluid W. The effective permeability kefO is obtained in a traditional manner, by a pressure build up test (block 13) in the reservoir 1. The pressure build-up test uses a pressure sensor 8 (FIG. 1A) located in the well 3. This pressure sensor 8 is linked to a device 9 for controlling and processing the signals it sends back, located for example at a well head. Device 9 may also control the network of electrodes 5 and process the signals it sends back.

Before carrying out the test, the reservoir 1 produces one of the fluids O. The production is obtained by a production well, which may or not be different to the well used for the measurements. In FIG. 1A, there is only one well 3 shown and it is assumed that it is used for measurements, production and injection. The pressure build up test, is performed by first stopping the production of the reservoir. The production well is closed and the variation in the pressure at the pressure sensor 8 is measured over time. The interpretation of the pressure variation leads to the effective permeability kefO of the reservoir to fluid O at the residual saturation in another fluid W.

The dynamic model (block 20) for the flow of fluids in the reservoir is first initialised. This initialisation is done by inputting the basic values (block 21) of the relative permeability $(krO)_b$ and $(krW)_b$ to each of the fluids O and W as a function of the saturation S(W) in one of them W. These basic relative permeability values may be taken from the literature (block 22" in FIG. 6B). Collections of geological data exist in the literature for oil exploration areas. These collections can take the form of databases.

Values obtained by permeability tests (block 22) carried out in the laboratory using samples taken from core wells from the reservoir may also be used. The dynamic flow model is updated by modifying these relative permeability values until they coincide with the real values. In order to initialise the dynamic model (block 20), the data relating to the injection of one of the fluids, W when it is used, is also entered (block 23). This data includes the pressure p in the well 3 and/or its flow rate q. The pressure p information is measured by the pressure sensor 8.

To run the dynamic model at this stage, the flow rate q" and/or the pressure p" expected for the fluid O that is to be extracted in one or several possible production wells is needed. However, at this stage, the flow behaviour in the reservoir that this model is going to simulate (block 20) may not be very close to the real flow behaviour, due to the lack of precision in the basic relative permeability values $(krO)_b$, $(krW)_b$ that were fed in for the initialisation.

According to one embodiment of the process of the invention, the dynamic model is updated with intermediate relative permeability values $(krO)_i$, $(krW)_i$ that are closer and closer to the real values in the reservoir. The dynamic flow model is thus refined, and the resulting simulation will conform as closely as possible to the real behaviour of the reservoir. Accordingly, the process according to the embodiment of the invention described herein leads to obtaining variation in the relative permeability, as near as possible to that found in reality which may not be measured directly onsite.

The dynamic model generates a saturation distribution at block 24. Examples of distributions of relative permeability and resistivity are illustrated in FIGS. 5a-b, 6a-b. A comparison is made at block 40 between the saturation distribution obtained on the basis of a measurement (SDM) (block 30) for the reservoir and a simulated saturation distribution (SSD) generated by the dynamic model (block 24) for the reservoir. The SSD furnished by the dynamic model is of substantially the same nature as the SSM, appreciably under the same condition, in other words, it reflects the state of the reservoir at the moment of the measurement.

In one embodiment, the SDM (block 30) for the reservoir is obtained on the basis of a measurement of a physical property in the reservoir, such as voltage or current for example, made by the network (5) of electrodes located within the reservoir at the well 3. It should be understood by persons skilled in the art, that the measurement of the physical property may be made by means other than electrodes.

In order to obtain the SDM (block 30) of the reservoir, one begins by carrying out a basic measurement (block 31) in the well while it is producing one of the fluids O and before injecting another fluid W. One may, for example, measure the voltage at the terminals of the measurement electrodes 5-a and 5-b, while a current flows between the different feed and return electrode couples 5-1 and 5-2. One obtains a series of basic voltages. If the formation is homogenous over the whole depth of the reservoir, a single measurement will suffice by feeding in current between a single electrode couple.

After carrying out the basic measurement, one then injects the fluid W into the reservoir 1 via the well 3 (block 32). The injection flow rate q is known, and one measures the pressure p in the well as described previously, as well as the flow rates q" and pressures p" in any production wells. While this injection is being carried out, at a given moment, a routine measurement of the voltage at a given current is carried out. This given moment corresponds to a certain injection time for the fluid W (block 33). With the basic measurement and the routine measurement one obtains a useful measure (block 34) by subtraction. It is based on this useful measure that it is provided, directly or not, the SDM for the reservoir. Note that instead of carrying out voltage measurements at blocks 31 and 33, current measurements at a known voltage may be carried out.

From the useful measure (block 34), via a classical inversion routine (block 35), one obtains a measured resistivity distribution (block 36). Then, by applying the Archie formula (block 37), the measured saturation distribution SDM (block 38) is obtained. The Archie formula, well known to those skilled in the art, is an empirical formula that gives the resistivity of a formation containing at least one electrically conductive fluid as a function of the porosity of the formation, the saturation in this fluid and the resistivity of this fluid. It is using this SDM that the comparison will be carried out in block 40.

The SSD (block 24) is obtained from the dynamic model for flow (block 20) in the reservoir. A comparison (block 40) is then carried out, usually by way of a computer, between the SDM (block 30) and the SSD (block 24), appreciably under the same conditions. If the two distributions substantially coincide, it signifies that the variation in the relative permeability to at least one of the fluids O and W as a function of the saturation S(W) in one of the fluids W contained in the dynamic model corresponds to the real value for the reservoir (block 41). At this stage block 41 provides the final relative permeability values $(krO)_f$, $(krW)_f$. In this situation, the dynamic model obtained may be considered as sufficiently reliable and accurate. It may be used to simulate the behaviour of the reservoir in the future.

If the saturation distributions (blocks 23 and 30) do not coincide, the dynamic model (block 20) is further refined so that the behaviour that it is going to simulate comes closer to the real value for the reservoir. The dynamic flow model is updated with the intermediate relative permeability values $(krO)_i$, $(krW)_i$ to each of the fluids O and W as a function of the saturation S(W) in one of the fluids W (block 25). By using the dynamic flow model with the intermediate relative permeability values, $(krO)_i$, $(krW)_i$, a new simulated distribution is obtained and one repeats the comparison stage with the same SSD (block 30). Updating is done by changing, if necessary, several times the relative permeability values (block 25) until the simulated and measured saturation distributions coincide.

In order to gain more knowledge of the reservoir, it is preferable, when a substantial coincidence between SSD and SDM has been obtained with the SDM corresponding to a given moment, to repeat the steps from the measurements in order to obtain at least one other variation in the relative permeability and at least one fluid in other conditions. Accordingly, one takes another routine measurement at another given moment, this leads to another SDM. The dynamic model one works out another SSD, appreciably under the same conditions as the measured response, and the comparison stage is repeated until they substantially coincide. The repetition of the measurement stages over time makes it possible to make the dynamic flow model (block 20) even more reliable.

Figure 3A:
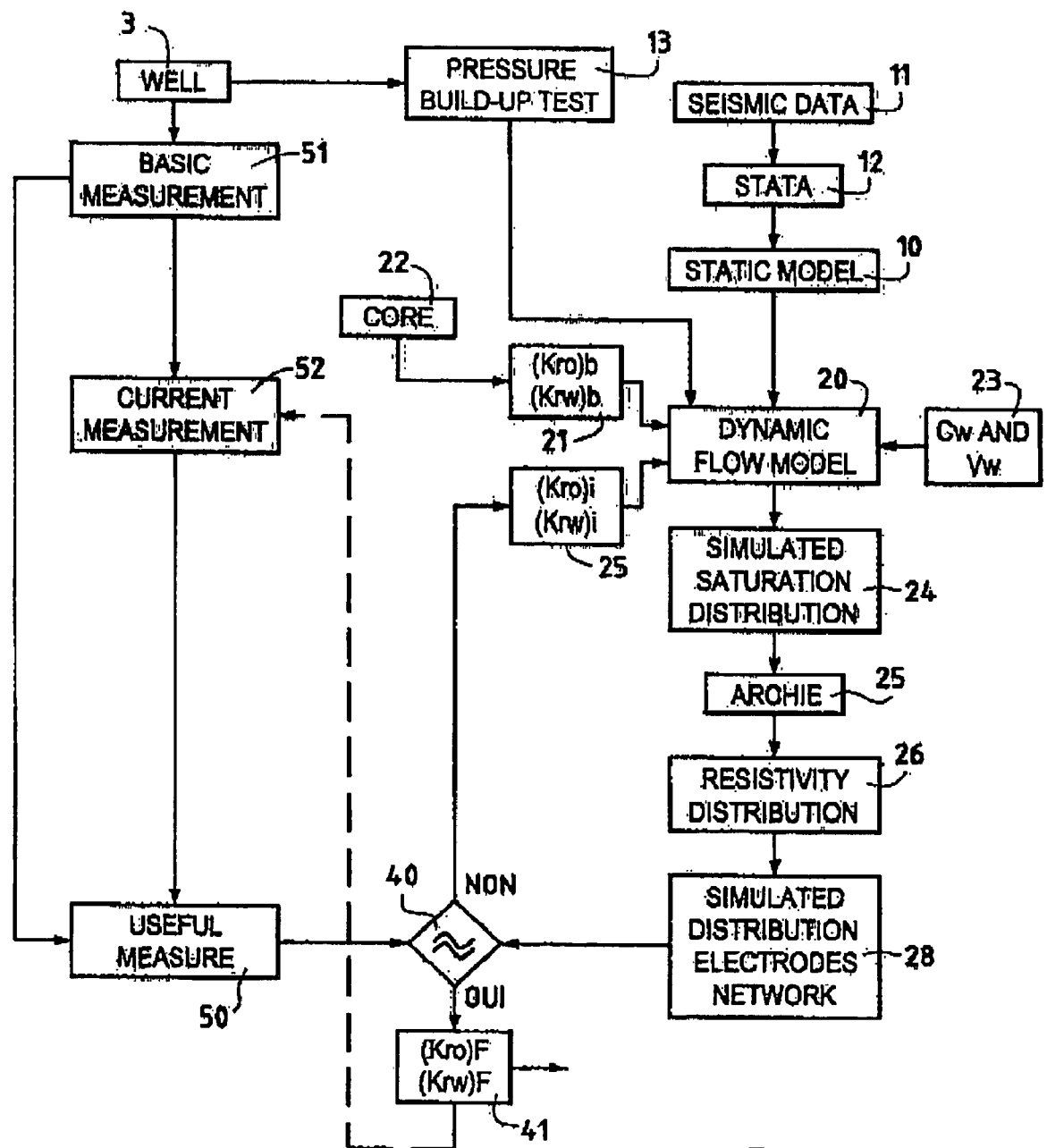
FIGS. 3A and 3B show two variations of the block diagram in FIG. 2.

Instead of the measured and simulated distributions being in terms of saturation, it is possible that these distributions may be in terms of voltage or current. It is also possible that there is no injection of one of the fluids into the reservoir. One of the fluids W may be present in the reservoir in the form of a groundwater table. Referring now to FIG. 3A. The measured response (block 50) may be obtained using measurements obtained via the network 5 of electrodes located in the well 3. On begins, as shown in the block diagram in FIG. 2, by carrying out a basic measurement in the well 3 (block 51). Then, a routine measurement is carried out while well 3 is producing one of the fluids O. This routine measurement is carried out at a given reference moment, for example from the basic measurement (block 52). A useful measure is deduced from this by subtracting the basic measurement from the routine measurement and it is this useful measure that constitutes the measured response (block 40) of the reservoir.

The dynamic model (block 20) is obtained from the static model (block 10) as described in FIG. 2. As there is no injection of fluid W, fluid W being found naturally in the form of a groundwater table, the dynamic model (block 20) is initialised with the compressibility $C_w$ of the fluid W and the volume $V_w$ of the groundwater table (block 23"). There is no change as regards its initialisation with the basic relative permeability values $(krO)_b$ and $(krW)_b$.

A simulated saturation model (block 24) is deduced from the dynamic flow model (block 20), as shown in FIG. 2. By applying the Archie formula (block 25) to the simulated saturation model, one obtains the simulated resistivity model (block 26) for the reservoir. One obtains a simulated response for the reservoir (block 28) in terms of voltage or current from the simulated resistivity model. This is done through the application of a simple analytical formula well known to those skilled in the art. A comparison is made in block 40 between the measured response and the simulated response appreciably under the same conditions. The following steps in the process are similar to those explained in connection with FIG. 2.

Figure 3B:
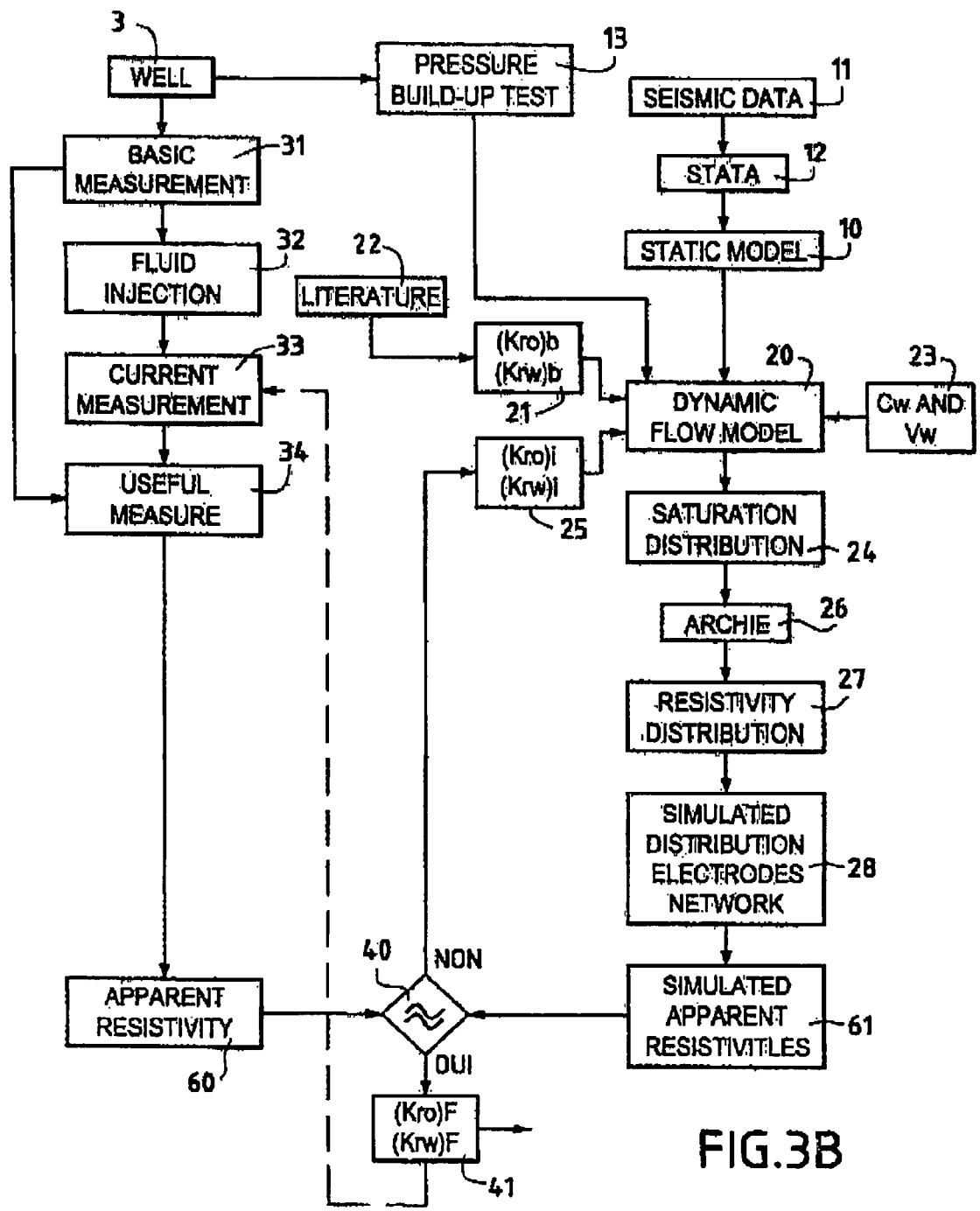

One could consider that the simulated response and the measured response are responses in terms of apparent resistivity. FIG. 3B illustrates this variation. This figure is comparable on the one hand to FIG. 2 and on the other hand to FIG. 3A. The measurements are carried out as shown on FIG. 2 with the injection of the fluid W. With the basic measurement (block 31) and the routine measurement (block 33), which may be made in terms of voltages, one obtains the useful measure (block 34) which may be as the measure obtained at block 34 of FIG. 2. By applying a simple analytical formula to the useful measure, similar to the inversion routine (block 35) in FIG. 2, one obtains the measured response of the reservoir in terms of the apparent resistivity (block 60). The simulated response of the dynamic model in terms of apparent resistivity (bock 61) is obtained from the simulated response of the network of electrodes (block 28 in FIG. 3A) to which one applies a simple analytical formula. Another difference in the block diagram shown in FIG. 3B compared to the block diagrams shown in FIGS. 2 or 3A is that the basic relative permeability values $(krO)_b$, $(krW)_b$ are now taken from the literature instead of tests on samples (block 22").

Figure 4:
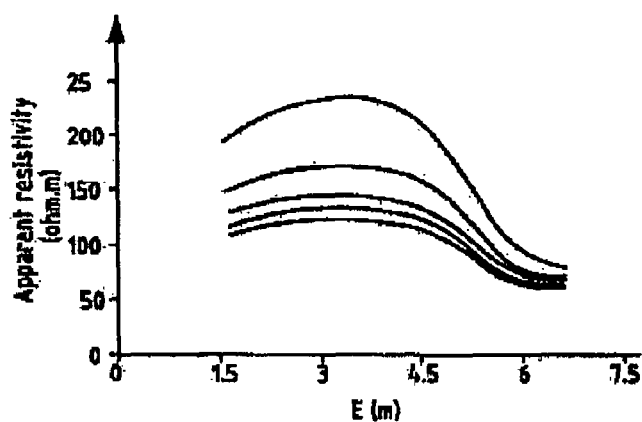
FIG. 4 shows several resistivity responses measured in the reservoir.

FIG. 4 shows five measured responses (distributions) in terms of the apparent resistivity of the reservoir at different distinct times, after the following injection times for fluid W:

T1=4 hours
T2=8 hours
T3=12 hours
T4=16 hours
T5=20 hours

One assumes that these responses have been obtained in a reservoir around 15 metres thick, equipped with a network of 14 electrodes, regularly spaced out along the whole depth of the reservoir. This reservoir has a basic resistivity of around 500 ohm.m. One injects, into the reservoir, a fluid W with an injection flow rate of around $9.2 \cdot 10^{-5}$ m³/s. By using the dynamic model, one expects the simulated responses, in terms of the apparent resistivity that it produces under conditions that correspond to the various times, to coincide with the measured responses.

Figure 5A:
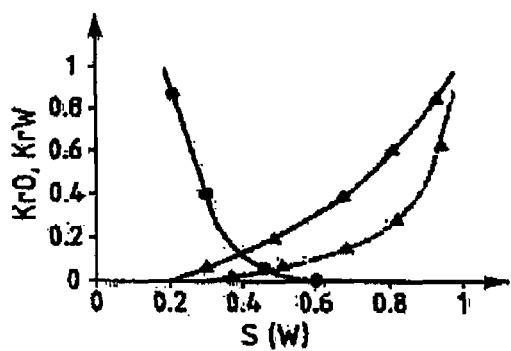
FIGS. 5A and 5B show relative basic permeability curves obtained after running the dynamic flow model.
Figure 5B:
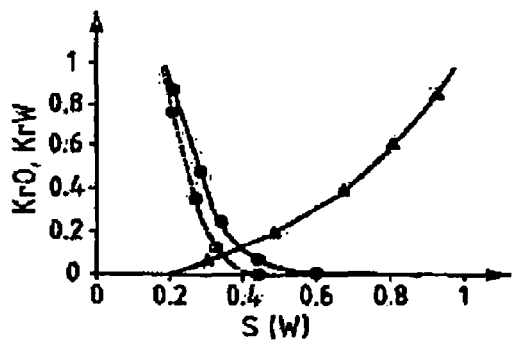

FIGS. 5A and 5B represent, respectively, a set of basic curves of the relative permeability krW to the fluid W (identified with the Δ symbols) and the relative permeability krO to the fluid O (identified with the • symbols) as a function of the saturation S(W) in fluid W in a reservoir. The curves with unbroken lines correspond to the basic relative permeability values. It is these values that are used to initialise the dynamic flow model. The broken line curves correspond to the intermediate values introduced when the model is updated, which lead to the convergence between the measured and simulated distributions of the reservoir for a measurement at a given time.

Figure 6A:
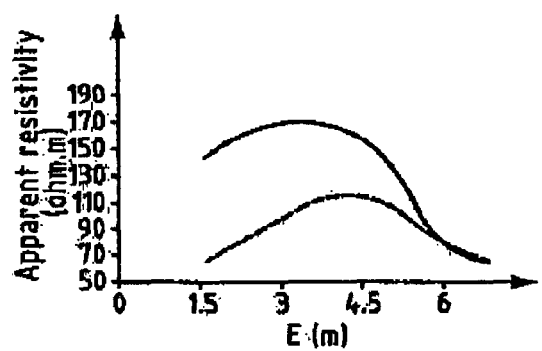
FIGS. 6A and 6B show the measured and simulated resistivity distributions obtained with the relative permeability curves from FIGS. 5A and 5B.
Figure 6B:
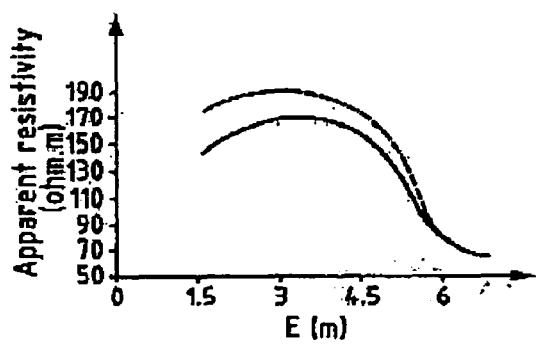

In FIGS. 6A and 6B, which should be examined in parallel with FIGS. 5A and 5B, the simulated distributions in terms of the apparent resistivity of the reservoir are shown as a function of the distance E between the electrodes that are involved in the circulation of current. The simulated distribution, shown as an unbroken line, is the first simulated distribution obtained, by using the process according to the invention, from the basic relative permeability values. The distribution, shown as a broken line, is the simulated distribution that substantially coincides with the measured distribution; it is obtained after several updates of the dynamic flow model. After the modification of the relative permeability values krW to the fluid W in FIG. 5A, the first simulated distribution in FIG. 6A has joined the measured distribution. In the same way, after the modification of the relative permeability values krO to the fluid O in FIG. 5B, the first simulated response in FIG. 6B has joined the measured distribution.

Although certain embodiments of the present invention have been represented and described in a detailed manner, it will be understood that different changes and modifications may be made, while remaining within the scope of the present invention.

The invention claimed is:

1. A process for refining a model of a reservoir containing fluids (W, O), the model having as an input an estimate of a relative permeability value (krO, krW) of at least one of the fluids in the reservoir as a function of the saturation of at least one of the fluids (W, O), the method comprising:
   (a) determining, for one of the fluids of the reservoir, a saturation distribution on the basis of a measurement (SDM) of a physical property in the reservoir;
   (b) creating a dynamic model for the flow of fluids in the reservoir;
   (c) generating a simulated saturation distribution (SSD) by the dynamic model;
   (d) comparing the SSD with the SDM; and (e) if it is determined from the comparing step d) that the SSD and SDM coincide the dynamic model is considered reliable and the relative permeability value is output, otherwise updating the dynamic model with an intermediate relative permeability value ($krO_i$, $krW_i$) and repeating steps (b) and (c).

2. The process of claim 1 further including, if the saturation distributions compared substantially coincide, setting the output relative permeability value (krO, krW) as being that which the dynamic model provides under the conditions of the SSD.

3. The process according to claim 1, in which, if the distributions coincide, steps (a) to (c) are repeated at least once, with the SDM being obtained at another given moment.

4. The process according to claim 1, whereby the basic relative permeability values $(krO)_b$ and $(krW)_b$ to said fluid are obtained from analyses carried out on geological samples taken from the reservoir.

5. The process according to claim 1, whereby the basic relative permeability values $(krO)_b$ and $(krW)_b$, are obtained from collections of data concerning the reservoir.

6. The process according to claim 1, whereby the SDM is determined on the basis of a resistivity distribution.

7. The process of claim 6 wherein the SDM is obtained from the resistivity distribution by applying Archie formula.

8. The process of claim 6 wherein the resistivity distribution is obtained from an inversion routine applied to electric parameters measured with a network of electrodes.

9. The process of claim 1 wherein the measurement comprises a basic measurement of the physical property in the reservoir.

10. The process of claim 8 wherein the measurement further comprises injection of a fluid (w) in the reservoir.

11. The process of claim 9 wherein the measurement further comprises a current measurement of the physical property in the reservoir.

12. The process of claim 1 wherein the physical property is a voltage potential.

13. A process for refining a model of a reservoir containing fluids (W, O), the model having as an input an estimate of a relative permeability value (krO, krW) of at least one of the fluids in the reservoir as a function of the saturation of at least one of the fluids (W, O), the method comprising:

(a) determining, for one of the fluids in the reservoir, a resistivity distribution on the basis of a measurement (RDM) of a physical property in the reservoir;

(b) creating a dynamic model for the flow of fluids in the reservoir;

(c) generating a simulated resistivity distribution (SRD) by the dynamic model;

(d) comparing the SRD with the RDM; and (e) if it is determined from the comparing step d) that the SSD and RDM coincide the dynamic model is considered reliable and the relative permeability value is output, otherwise updating the dynamic model with an intermediate relative permeability value ($krO_i$, $krW_i$) and repeating steps (b) and (c).

14. A computer-implemented process for determining, for a reservoir containing fluids (W, O), a dynamic flow model, the process comprising:

(a) determining, for one of the fluids of the reservoir, a saturation distribution on the basis of a measurement (SDM) of a physical property in the reservoir;

(b) creating a dynamic model for the flow of fluids in the reservoir on the basis of the variation in the relative permeability (krO, krW) of at least one of the fluids in the reservoir, as a function of the saturation of at least one of the fluid (W, O) obtained from a measurement of a core from the reservoir;

(a) generating a simulated saturation distribution (SSD) by the dynamic model;

(d) comparing the SSD with the SDM; and (e) if it is determined from the comparing step d) that the SSD and SDM coincide the dynamic model is considered reliable and the variation in the relative permeability is output or store as a final value, otherwise updating the dynamic model with an intermediate relative permeability value ($krO_i$, $krW_i$) and repeating steps (b) and (c).

* * * * *